US 6,725,801 B1

(12) United States Patent
Carrington et al.

(10) Patent No.: US 6,725,801 B1
(45) Date of Patent: Apr. 27, 2004

(54) MULTIPLE MOUNT FINGERPRINT INK DISPENSER

(76) Inventors: John H. Carrington, 2316 Wakefield Plantation Rd., Raleigh, NC (US) 27614; David W. Harvey, 1450 Long Mill Rd., Youngsville, NC (US) 27596

( * ) Notice: Subject to any disclaimer, the term of this patent is extended or adjusted under 35 U.S.C. 154(b) by 155 days.

(21) Appl. No.: 10/298,296

(22) Filed: Nov. 18, 2002

(51) Int. Cl.[7] .................................................. B41K 1/38
(52) U.S. Cl. ........................ 118/31.5; 206/568; 206/225
(58) Field of Search ............................... 118/31.5; 427/1; 206/568, 225

(56) References Cited

U.S. PATENT DOCUMENTS 1,538,767 A * 5/1925 Watson ..................... 118/31.5
5,398,812 A * 3/1995 Hwang ....................... 206/568

* cited by examiner

Primary Examiner—Laura Edwards

(57) ABSTRACT

A fingerprint ink dispenser includes a one-piece clamshell pocket sized case including base and pivotal lid that overlies the base. The base holds a fingerprint inkpad and includes provisions for mechanically, frictionally and magnetically mounting the case on a variety of mounting surfaces.

2 Claims, 4 Drawing Sheets

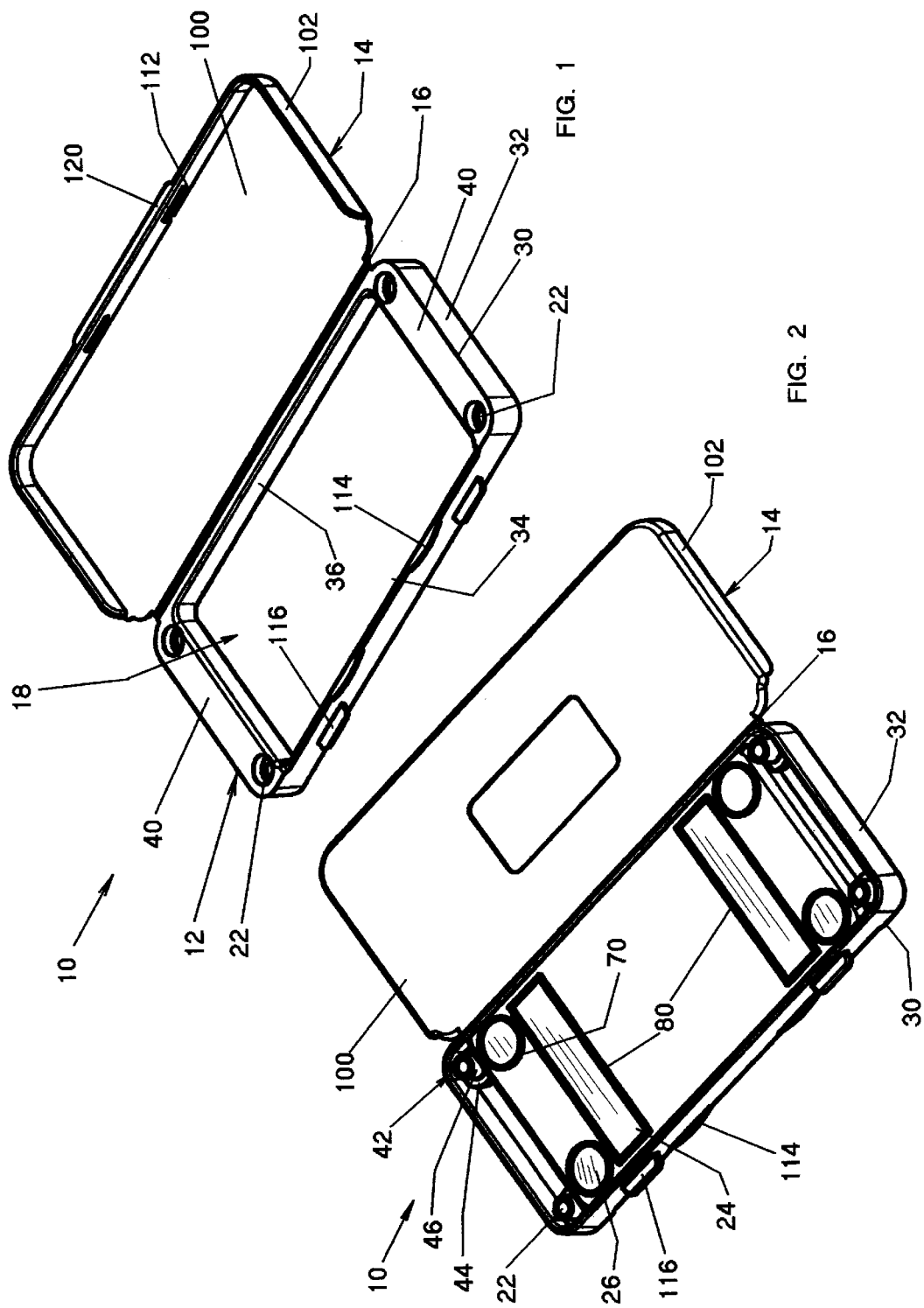

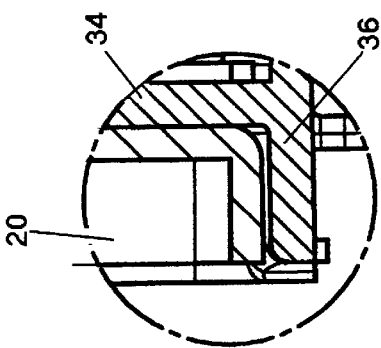
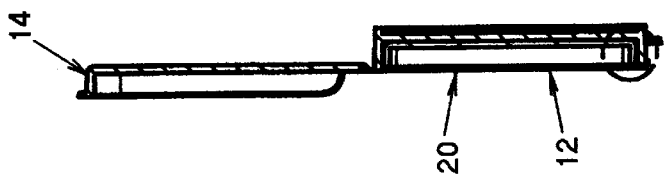
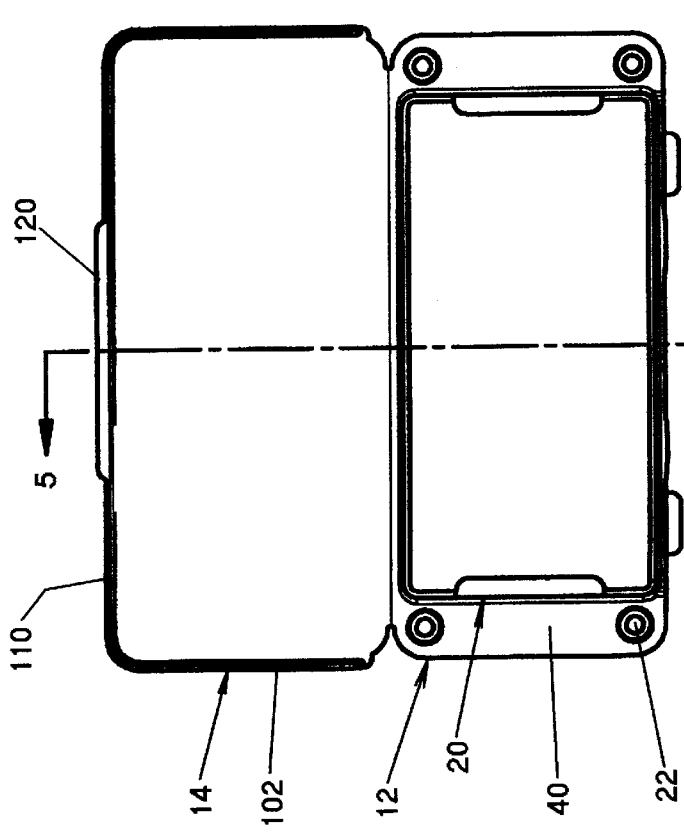
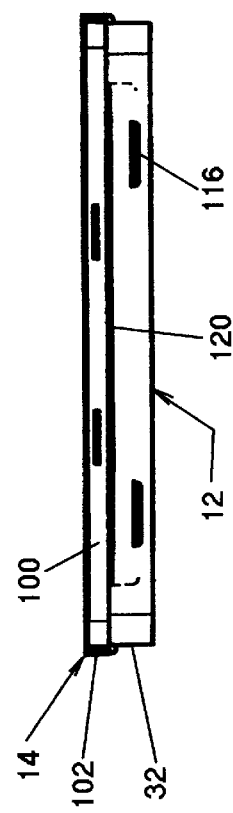

ns**

MULTIPLE MOUNT FINGERPRINT INK DISPENSER

FIELD OF THE INVENTION

The present invention relates to fingerprinting apparatus, and, in particular, to a fingerprint ink dispenser that may be mounted at site of use on varying substrates.

BACKGROUND OF THE INVENTION

Fingerprinting is commonly employed for identifying individuals in many investigative situations. The situations requiring the procedure may vary from fixed departmental locations to mobile and transient sites. Accordingly, a variety of dispensers have been developed tailored for addressing the multiplicity of conditions.

For field use, fingerprint cases adapted to be pocket carried are commonly used. For desk or other permanent locations, brackets are used to fixedly mount the applicator pad and case. For single print and mobile applications, smaller cases and pads are preferred.

The resultant variety of dispensers, sizes and mounting techniques result in a multitude of designs, even within a single organization and often at a compromise to the underlying task, i.e. reliably contemporaneously taking the necessary prints, in a quality format.

In view of the foregoing limitations, it would be desirable to provide a single fingerprint case and pad design that could be used in all fingerprinting venues and reliably deployed for taking the necessary prints for the investigations at hand.

BRIEF SUMMARY OF THE INVENTION

The present invention provides a fingerprinting apparatus having a one-piece clamshell case carrying a fingerprint pad in a base and having an integrally hinged overlapping lid. The base is provided with plural mounting modes. First, the base includes fastener holes for allowing fixed attachment of the case at a permanent site. The lower surface of the base provides located attachments of magnetic and slip resistant pads allowing the case to be used on a variety of transiently available surfaces. All mounting modes are within the confines of a typical pocket envelop, facilitating convenient carrying to remote and mobile sites, thereby allowing a single design to be utilized for the preponderance of investigative occurrences.

Accordingly, it is an object of fingerprint ink dispenser that may be deployed in a plurality of mounting modes.

Another object of the invention is to provide a fingerprinting pad and case that permits permanent and releasable mounting.

A further object is to provide a single format fingerprinting pad and case that may be mechanically, adhesively or frictionally mounted on a working surface for securing fingerprints.

DESCRIPTION OF THE DRAWINGS

The above and other objects and advantages of the present invention will become apparent upon reading the following detailed description taken in conjunction with the accompanying drawings in which:

FIG. 1 is a top perspective view of a multiple mount fingerprint ink dispenser, without the finger print pad, in accordance with a preferred embodiment of the invention;

FIG. 2 is a bottom perspective view of the pad case of FIG. 1;

FIG. 3 is a front view of the pad case in the closed position;

FIG. 4 is a top view of the pad case in the open position;

FIG. 5 is a cross sectional view of the pad case taken along line 5—5 in FIG. 4;

FIG. 6 is an enlarged fragmentary cross sectional view illustrating the circled area in FIG. 5;

DETAILED DESCRIPTION OF THE PREFERRED EMBODIMENTS

Figure 7:
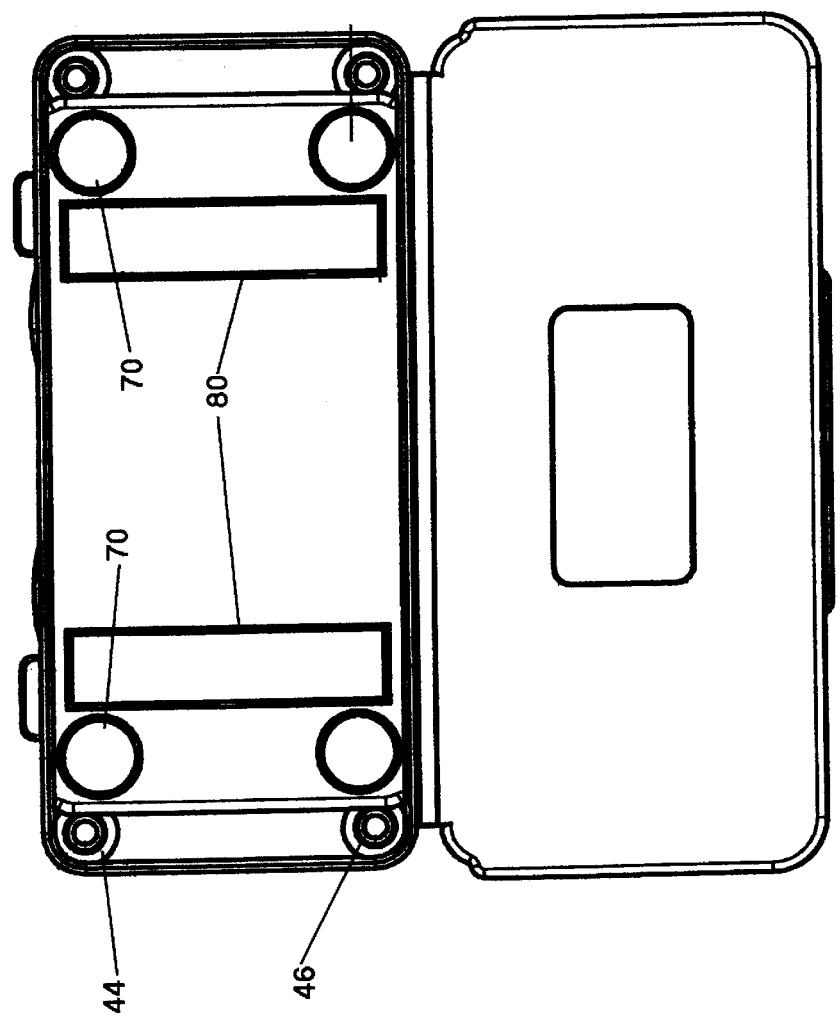
FIG. 7 is a bottom view of the dispenser showing the three available mounting modes.

Referring to the drawings for the purpose of describing the preferred embodiment and not for limiting same, FIGS. 1 through 3 a multiple mount fingerprint ink dispenser 10 comprising a pocket size case including a one-piece clam shell base 12 and cover 14 interconnected by a integral living hinge 16 permitting movement between the open position shown in FIGS. 1 and 2 and the closed position shown in FIG. 3. The base 12 includes an upwardly opening rectangular cavity 18 for retaining a fingerprint pad 20 for enabling the inking of fingerprints when the case is positioned in an imprinting position, which as described below is facilitated by mechanical mounting using fastener holes 22 located at the lateral edges, adhesive/magnetic mounting using connector strips 24 located on the lower surface of the base 12, or frictional mounting using slip resistant pads 26 located at the lower corners or the base, as well as conveniently pocket carried for transient use.

The case of the dispenser 10 is an injection molded article preferably a high strength plastic material. The pad 20 comprises a micro reticulated carrier impregnated with fingerprint ink. Plastic and ceramic carriers are generally preferred. A suitable pad is available as model number AFPT268A from Sirche Fingerprint Laboratories Inc., assignee of the present invention.

The base 12 includes a generally rectangular top wall 30 circumscribed by a downwardly depending peripheral rim 32 having a lower surface parallel to the top wall 30. The cavity 18 is generally rectangular and laterally centered in the top wall 30 and defined horizontally by a bottom wall 34, spaced intermediate the lower surface of the rim 32 and the top wall 30, and a peripheral sidewall 36, the inner surface of which conformably frictionally receives and retains the fingerprint pad 20.

Figure 8:
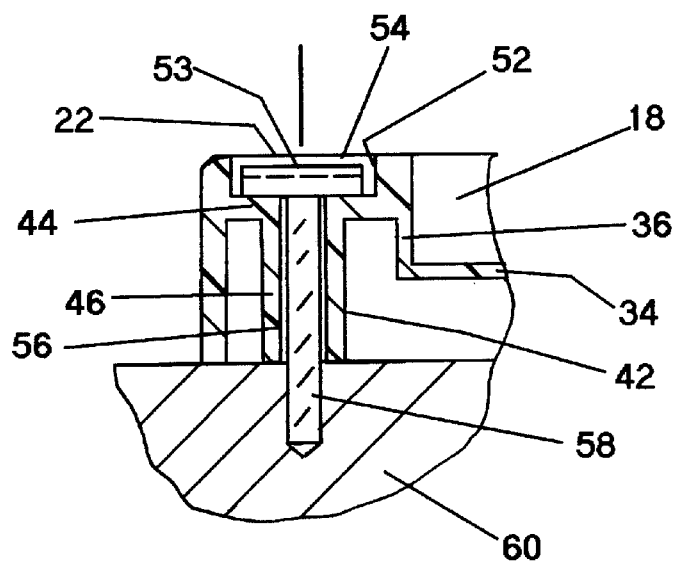
FIG. 8 is a fragmentary view illustrating the fastener mount mode of the pad case.
Figure 9:
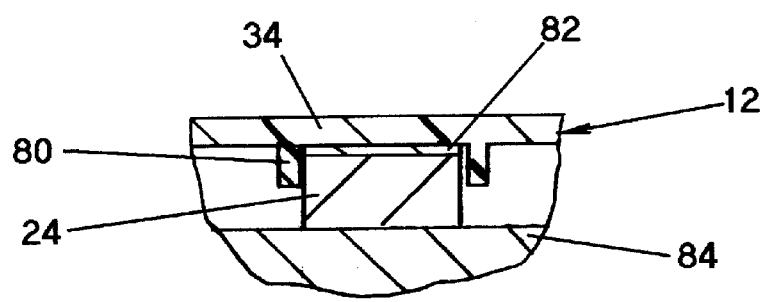
FIG. 9 is a fragmentary view illustrating the magnetic mount mode of the pad case.
Figure 10:
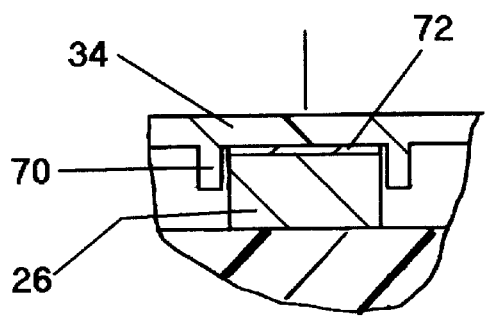
FIG. 10 is a fragmentary view illustrating the slip resistant mount mode of the pad case.

The top wall 30 includes lateral flanges 40 extending between the rim 32 and the cavity 18. A pair of transversely spaced fastener sleeves 42 are formed at the lower surface of each of the flanges 40 as shown in FIGS. 2 and 8. Each sleeve 42 includes a head section 44 and a coaxial shank section 46. A multiple step fastener hole 22 is formed coaxially in and extends vertically through each sleeve. The holes 22 each include a counterbore 52 for receiving below the top wall 30 the head 53 of a mounting fastener 54 and a bore 56 for receiving the threaded shank 58 for mechanically attaching the base of the case 10 to a mounting surface 60 in a horizontal, vertical or inclined position.

Downwardly projecting mounting rings 70 are formed at the lower surface of the cavity bottom wall and terminate at or slightly above the rim. The pads 26 include an adhesive backing 72 and a slip resistant bottom surface. The pads 26 are mounted interior of the rings 70. The pads 26 allow the case to be mounted on a convenient surface and resist operational movement during application of the fingerprint ink.

A pair of rectangular shaped downwardly projecting ridges 80 are formed at the lower surface of the cavity bottom wall inwardly of the rings 70 and oriented transversely between the front and rear walls of the rim 30. Rectangular flexible magnetic strips 24 having an adhesive backing 82 are attached within the confines of the ridges 80. The magnetic strips 24 allow the case to be mounted for use on ferrous-based materials regardless of inclination.

The cover 14 includes a top wall 100 overlying the top wall of the base 12 in the closed position. The top wall 100 includes a U-shaped lip 102 slidably surrounding the front and sidewalls of the rim in the closed position. In a conventional manner, the hinge section 16 upon initial closure is stressed to establish thereacross a horizontal hinge axis. In the closed position, the exterior surfaces provide a smooth envelope for pocket carrying of the dispenser.

The front wall 110 of the lip 102 includes a first pair of laterally spaced slots 112 recessed in the rear surface thereof. The front wall of the rim 30 includes a first pair of laterally spaced, frontally projecting tabs 114 that enter and detent with the slots 112 to maintain the closed position. The front wall of the rim 30 includes a second pair of laterally spaced tabs 116 outwardly of the tabs 114. A frontally projecting ledge 120 is formed at the lower edge of the front wall of the lip 102. A user may digitally engage the tabs 116 and the ledge 120 to release the cover 14 from the detented closed position.

In preferred format, the case 10 is about 6 inches long, 3 inches wide and 0.5 inches thick, presenting an envelope permitting the case to be transported from site to site, conveniently, in an available pocket or case. For transient site work, the friction and magnetic interfaces permit deployment on a variety of substrates. For stationary use, the mechanical fastening mounting may be employed. Accordingly, rather than relying on a plurality of fingerprinting cases for ordinary use, the present invention provides a single case design useable for all commonly encountered situations within a fingerprinting organization.

Having thus described a presently preferred embodiment of the present invention, it will now be appreciated that the objects of the invention have been fully achieved, and it will be understood by those skilled in the art that many changes in construction and widely differing embodiments and applications of the invention will suggest themselves without departing from the sprit and scope of the present invention. The disclosures and description herein are intended to be illustrative and are not in any sense limiting of the invention, which is defined solely in accordance with the following claims.

What is claimed:

1. A fingerprint ink dispenser comprising: a one-piece casing member formed of a plastic material and including a base member and a lid member pivotally connected by an integral hinge for relative movement between an open position and a closed position, detent means on said base member and said lid member for releasably maintaining said closed position, said base member having a generally rectangular planar top wall surrounded by a downwardly depending rim; an upwardly opening generally rectangular cavity formed in and laterally centered on said top wall and defining laterally spaced flange areas with said rim, said cavity including a bottom wall spaced below said top wall and a peripheral side wall interconnecting said top wall and said bottom wall; a fingerprint ink dispensing pad carried in said cavity; tubular fastener sleeves projecting downwardly from said flange areas adjacent corners of said base, each of said sleeves including a counterbore opening at said top wall for receiving the head of a fastener and a lower bore for receiving a threaded shank of the fastener for mechanically mounting said base on a substrate; circular rims formed on said bottom wall of said cavity adjacent the corners thereof for receiving slip resistance pad members therewithin; and a pair of laterally spaced rectangular ridges formed on said bottom wall of said cavity for receiving magnetic strips for magnetically attaching said base to a ferrous substrate.

2. A case for dispensing fingerprint ink from a pad containing releasable fingerprinting ink comprising: a base member; a lid member; hinge means pivotally connecting said lid member to said base member for movement between an open position and a closed position, said base member having a top wall surrounded by a downwardly depending rim; depression means formed in said top wall defining a receptacle for retaining said ink pad; apertures in said top wall between said depression means and said rim for receiving threaded fasteners for connecting said base member to a mounting surface; and a plurality of downwardly projecting surfaces formed in said wall defining a cavity for retaining pad means for releasably frictionally holding said base member on the mounting surface.

\* \* \* \* \*